United States Patent [19]
Gaffar

[11] Patent Number: 5,296,214
[45] Date of Patent: * Mar. 22, 1994

[54] ANTICALCULUS COMPOSITION

[75] Inventor: Abdul Gaffar, Princeton, N.J.

[73] Assignee: Colgate-Palmolive Co., New York, N.Y.

[*] Notice: The portion of the term of this patent subsequent to May 4, 2010 has been disclaimed.

[21] Appl. No.: 925,363

[22] Filed: Aug. 4, 1992

Related U.S. Application Data

[63] Continuation-in-part of Ser. No. 754,887, Sep. 6, 1991, Pat. No. 5,192,530, and a continuation-in-part of Ser. No. 655,571, Feb. 14, 1991, Pat. No. 5,178,851, and a continuation-in-part of Ser. No. 758,345, Sep. 9, 1991, Pat. No. 5,192,531, and a continuation-in-part of Ser. No. 398,592, Aug. 28, 1989, Pat. No. 5,188,821, and a continuation-in-part of Ser. No. 657,885, Feb. 19, 1991, Pat. No. 5,180,578, said Ser. No. 657,885, is a continuation of Ser. No. 398,605, Aug. 25, 1989, abandoned, Ser. No. 754,887, Aug. 25, 1989, which is a continuation of Ser. No. 398,606, Aug. 25, 1989, abandoned, Ser. No. 655,571, Aug. 25, 1989, which is a continuation of Ser. No. 398,566, Aug. 28, 1989, Pat. No. 5,032,386, Ser. No. 758,345, Aug. 28, 1989, which is a continuation of Ser. No. 399,669, Aug. 25, 1989, abandoned.

[51] Int. Cl.$^5$ .................. A61K 7/16; A61K 7/15

[52] U.S. Cl. .............................................. 424/49

[58] Field of Search .................................. 424/49.58

[56] References Cited

U.S. PATENT DOCUMENTS

| | | | |
|---|---|---|---|
| 4,342,857 | 8/1982 | Gaffar | 424/49 |
| 4,427,652 | 1/1984 | Gaffar | 424/49 |
| 4,528,179 | 7/1985 | Gaffar | 424/49 |
| 4,816,245 | 3/1989 | Gaffar | 424/57 |
| 5,208,009 | 5/1993 | Gaffar et al. | 424/49 |

FOREIGN PATENT DOCUMENTS

| | | |
|---|---|---|
| 2090265 | 7/1982 | United Kingdom . |
| 2151478 | 7/1985 | United Kingdom . |
| 2224204 | 5/1990 | United Kingdom . |

*Primary Examiner*—Shep K. Rose
*Attorney, Agent, or Firm*—Robert L. Stone; Murray M. Grill

[57] ABSTRACT

An oral composition such as a dentifrice or mouthwash, comprises an effective antiplaque amount of a substantially water-insoluble noncationic antibacterial agents, such as 2,4,4-trichloro-2'-hydroxy-diphenyl ether (Triclosan) and polyvinyl phosphonate antibacterial-enhancing agent which enhances the delivery of said antibacterial agent to oral surfaces.

25 Claims, No Drawings

ANTICALCULUS COMPOSITION

This application is a continuation-in-part of application Ser. No. 07/754,887 filed Sep. 6, 1991, now U.S. Pat. No. 5,192,530, issued Mar. 9, 1993, which is a continuation of Ser. No. 07/398,606 filed Aug. 25, 1989, now abandoned; a continuation-in-part of application Ser. No. 07/655,571, filed Feb. 14, 1991, now U.S. Pat. No. 5,178,851, issued Jan. 12, 1993, which is a continuation of application Ser. No. 07/398,566 filed Aug. 28, 1989, now U.S. Pat. No. 5,032,386, issued Jul. 16, 1991; a continuation-in-part of application Ser. No. 07/758,345, filed Sep. 9, 1991, now U.S. Pat. No. 5,192,531, issued Mar. 9, 1993, which is a continuation of Ser. No. 07/399,669, filed Aug. 25, 1989, now abandoned; a continuation-in-part of application Ser. No. 07/398,592, filed Aug. 28, 1998, now U.S. Pat. No. 5,188,821, issued Feb. 23, 1993, and a continuation-in-part of application Ser. No. 07/657,885, filed Feb. 19, 1991, now U.S. Pat. No. 5,180,578, issue Jan. 19, 1993, which is a continuation of application Ser. No. 07/398,605, filed Aug. 25, 1989, now abandoned.

This invention relates to an antibacterial antiplaque oral compositions such as dentifrices and mouthwashes. More particularly, it relates to oral compositions containing a substantially water-insoluble noncationic antibacterial agent effective to inhibit plaque.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurrence of gingivitis.

Accordingly, it is highly desirable to include antimicrobial agents which have been known to reduce plaque in oral compositions. Frequently, cationic antibacterial agents have been suggested. Moreover, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic materials such as guanides and quaternary ammonium compounds as well as non-cationic compounds such as halogenated salicylanilides and halogenated hydroxydiphenyl ethers. The noncationic antibacterial antiplaque halogenated hydroxydiphenyl ether, triclosan, has also been described in combination with zinc citrate trihydrate in European Patent 0161,899 to Saxton et al. Triclosan is also disclosed in European Patent Publication 0271,332 to Davis as a toothpaste component containing a solubilizing agent such as propylene glycol and in PCT Publication WD 92/00721 to Read in combination with azacycloalkane diphosphonates.

The cationic antibacterial materials such as chlorhexidine, benzthonium chloride and cetyl pyridinium chloride have been the subject of greatest investigation as antibacterial antiplaque agents. However, they are generally not effective when used with anionic materials. Noncationic antibacterial materials, on the other hand, can be compatible with anionic components in an oral composition.

However, oral compositions typically are mixtures of numerous components and even such typically neutral materials as humectants can affect performance of such compositions.

Moreover, even noncationic antibacterial agents may have limited antiplaque effectiveness with commonly used materials such as polyphosphate anticalculus agents which are disclosed together in British Patent Publication 22 00551 of Gaffar et al and in EP 0251591 of Jackson et al.

It is an advantage of this invention that an oral composition is provided comprising a substantially water insoluble noncationic antibacterial agent wherein polyvinyl phosphonate (PVPA) enhances the antibacterial effect of the antibacterial agent to inhibit plaque formation, wherein the oral composition contains an orally acceptable liquid vehicle effective to enable said antibacterial agent to dissolve in saliva in effective antiplaque amount.

It is a further advantage of this invention that an antiplaque oral composition is provided which is effective to reduce the occurrence of gingivitis.

Additional advantages of this invention will be apparent from consideration of the following specification.

In accordance with certain of its aspects, this invention relates to an oral composition comprising an effective antiplaque amount of a substantially water insoluble noncationic antibacterial agent, at least about 0.005% by weight of polyvinyl phosphonate having recurring groups

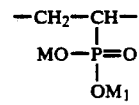

and average molecular weight of at least about 1,000 and wherein M and $M_1$ are hydrogen, alkali metal or ammonium and wherein M and $M_1$ are the same or different and an orally acceptable vehicle comprising at least one of a surface-active agent or a flavoring oil effective to enable said antibacterial agent to dissolve in saliva in effective antiplaque amount.

Typical examples of water insoluble noncationic antibacterial agents which are particularly desirable from considerations of antiplaque effectiveness, safety and formulation are:

Halogenated Diphenyl Ethers 2,4,4'-trichloro-2'-hydroxy-diphenyl ether (Triclosan)
2,2'-dihydroxy-5,5'-dibromo-diphenyl ether Halogenated Salicylanilides 4',5'-dibromosalicylanilide
3,4,5,'-trichlorosalcylanilide
3,4,5-tribromosalicylanilide
2,3,3',5-tetrachlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoromethyl salicylanilide (Fluorphene)

Benzoic Esters

Methyl-p-Hydroxybenzoic Ester
Ethyl-p-Hydroxybenzoic Ester
Propyl-p-Hydroxybenzoic Ester
Butyl-p-Hydroxybenzoic Ester Halogenated Carbanilides 3,4,4'-trichlorocarbanilide 2-trifluormethyl-4,4'-dichlorcarbanilide
3,3,4'-trichlorocarbanilide Phenolic Compounds (including phenol and its homoglogs, mono- and poly-alkyl and aromatic halo (e.g., Cl, Br, I)-phenols, resorcinol and catechol and their derivatives and bisphenolic compounds). Such compounds include inter alia:

| Phenol and its Homlogs | |
|---|---|
| Phenol | |
| 2-Methyl | -Phenol |
| 3-Methyl | -Phenol |
| 4-Methyl | -Phenol |
| 4-Ethyl | -Phenol |
| 2,4-Dimethyl | -Phenol |
| 2,5-Dimethyl | -Phenol |
| 3,4-Dimethyl | -Phenol |
| 2,6-Dimethyl | -Phenol |
| 4-n-Propyl | -Phenol |
| 4-n-Butyl | -Phenol |
| 4-n-Amyl | -Phenol |
| 4-tert-Amyl | -Phenol |
| 4-n-Hexyl | -Phenol |
| 4-n-Heptyl | -Phenol |
| 2-Methoxy-(2-Propenyl)-Phenol (Eugenol) | |
| 2-Isopropyl-5-Methyl-Phenol (Thymol) | |
| Mono- and Poly-Alkyl and Aromatic Halophenols | |
| Methyl | -p-Chlorophenol |
| Ethyl | -p-Chlorophenol |
| n-Propyl | -p-Chlorophenol |
| n-Butyl | -p-Chlorophenol |
| n-Amyl | -p-Chlorophenol |
| n-Hexyl | -p-Chlorophenol |
| Cyclohexyl | -p-Chlorophenol |
| n-Heptyl | -p Chlorophenol |
| n-Octyl | -p-Chlorophenol |
| O-Chlorophenol | |
| Methyl | -o-Chlorophenol |
| Ethyl | -o-Chlorophenol |
| n-Propyl | -o-Chlorophenol |
| n-Butyl | -o-Chlorophenol |
| n-Amyl | -o-Chlorophenol |
| Tert-Amyl | -o-Chlorophenol |
| n-Hexyl | -o-Chlorophenol |
| n-Heptyl | -o-Chlorophenol |
| p-Chlorophenol | |
| o-Benzyl | -p-Chlorophenol |
| o-Benzyl-m-methyl | -p-Chlorophenol |
| o-Benzyl-m-m-dimethyl | -p-Chlorophenol |
| o-Phenylethyl | -p-Chlorophenol |
| o-Phenylethyl-m-methyl | -p-Chlorophenol |
| 3-Methyl | -p-Chlorophenol |
| 3,5-Dimethyl | -p-Chlorophenol |
| 6-Ethyl-3-methyl | -p-Chlorophenol |
| 6-n-Propyl-3-methyl | -p-Chlorophenol |
| 6-iso-Propyl-3-methyl | -p-Chlorophenol |
| 2-Ethyl-3,5-dimethyl | -p-Chlorophenol |
| 6-sec Butyl-3-methyl | -p-Chlorophenol |
| 2-iso-Propyl-3-5-methyl | -p-Chlorophenol |
| 6-Diethylmethyl-3-methyl | -p-Chlorophenol |
| 6-iso-Propyl-2-ethyl-3-methyl | -p-Chlorophenol |
| 2-sec amyl-3,5-dimethyl | -p-Chlorophenol |
| 2-Diethylmethyl-3,5-dimethyl | -p-Chlorophenol |
| 6-sec Octyl-3-methyl | -p-Chlorophenol |
| p-Bromophenol | |
| Methyl | -p-Bromophenol |
| Ethyl | -p-Bromophenol |
| n-Propyl | -p-Bromophenol |
| n-Butyl | -p-Bromophenol |
| n-Amyl | -p-Bromophenol |
| sec-Amyl | -p-Bromophenol |
| n-Hexyl | -p-Bromophenol |
| Cyclohexyl | -p-Bromophenol |
| o-Bromophenol | |
| Tert-Amyl | -o-Bromophenol |
| n-Hexyl | -o-Bromophenol |
| n-Propyl-m,m-Dimethyl | -o-Bromophenol |
| 2-Phenyl Phenol | |
| 4-chloro-2-methyl phenol | |
| 4-chloro-3-methyl phenol | |
| 4-chloro 3,5-dimethyl phenol | |
| 2,4-dichloro-3,5-dimethylphenol | |
| 3,4,5,6-terabromo-2-methylphenol | |
| 5-methyl-2-pentylphenol | |
| 4-isopropyl-3-methylphenol | |
| 5-chloro-2-hydroxydiphenylmethane | |
| Resorcinol and Its Derivatives | |
| Resorcinol | |
| Methyl | -Resorcinol |
| Ethyl | -Resorcinol |
| n-Propyl | -Resorcinol |
| n-Butyl | -Resorcinol |
| n-Amyl | -Resorcinol |
| n-Hexyl | -Resorcinol |
| n-Heptyl | -Resorcinol |
| n-Octyl | -Resorcinol |
| n-Nonyl | -Resorcinol |
| Phenyl | -Resorcinol |
| Benzyl | -Resorcinol |
| Phenylethyl | -Resorcinol |
| Phenylpropyl | -Resorcinol |
| p-Chlorobenzyl | -Resorcinol |
| 5-Chloro | -2,4-Dihydroxydiphenyl Methane |
| 4'-Chloro | -2,4-Dihydroxydiphenyl Methane |
| 5-Bromo | -2,4-Dihydrocydiphenyl Methane |
| 4'-Bromo | -2,4-Dihydroxydiphenyl Methane |
| Bisphenolic Compounds | |
| 2,2'-methylene bis (4-chlorophenol) | |
| 2,2'-methylene bis (3,4,6-trichlorophenol) (hexachlorophene) | |
| 2,2'-methylene bis (4-chloro-6-bromophenol) | |
| bis (2-hydroxy-3,5-dichlorophenyl) sulfide | |
| bis (2-hydroxy-5-chlorobenzyl) sulfide | |

The noncationic antibacterial agent is present in the composition of the present invention in an effective antiplaque amount, preferably about 0.01–5% by weight, more preferably about 0.25–0.5% or about 0.05 to less than 0.5% and most preferably about 0.25–0.35%, e.g. about 0.3% in a dentifrice or preferably about 0.01–0.3% by weight, most preferably about 0.03–0.1% in a mouthwash or liquid dentifrice. The antibacterial agent is substantially water-insoluble, meaning that its solubility is less than about 1% by weight in water at 25° C. and even may be less than about 0.1%.

The preferred halogenated diphenyl ether is triclosan. The preferred phenolic compounds are phenol, thymol, eugenol, and 2,2-methylene bis(4-chloro-6-bromophenol). Triclosan is disclosed in aformentioned U.S. Pat. No. 4,022,880 as an antibacterial agent in combination with an anticalculus agent which provides zinc ions and in German Patent Disclosure 3,532,860 in combination with a copper compound. In European Patent Disclosure 0278,744 it is disclosed in combination with a tooth desensitizing agent containing a source of potassium ion. It is also disclosed as an antiplaque agent in a dentifrice formulated to contain a lamellar liquid crystal surfactant phase having a lamellar spacing of less than 6.0 nm and which may optionally contain a zinc salt in published European Patent Application 0161898 of Lane et al and in a dentifrice containing zinc citrate trihydrate in published European Patent Application 0161899 to Saxton et al.

In the ancestor application of the present application, antibacterial-enhancing agent (AEA) which enhances delivery of the antibacterial agent to, and retention thereof on, oral surfaces is described as distinct from poly(vinyl phosphonic acid) (PVPA) of the formula

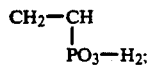

which, although being an AEA, does not contain a retention enhancing group. The presently claimed invention is directed to the presence of PVPA, an AEA, which, as indicated, does not contain a retention enhancing group but, nevertheless, enhances antibacterial inhibition of plaque and gingivitis. PVPA is employed in amounts effective to achieve antibacterial enhancement, typically within the range in the oral composition of about 0.005% to about 4%, preferably about 0.1% to about 3%, more preferably about 0.5% to about 2.5% by weight.

PVPA, employed herein, typically has an average molecular weight of about 1,000 to about 1,000,000. Molecular weight values given for such polyvinyl phosphonates are obtained from viscosity or light scattering measurements.

Synthetic anionic polyvinyl phosphonates have been previously disclosed as anticalculus agents per se in, U.S. Pat. No. 3,429,963 to Shedlovsky. However, that patent does not disclose use of such polyvinyl phosphonate agent for enhancing antibacterial activity.

PVPA contains phosphonic groups which enhance delivery of antibacterial agent to the teeth and soft gum tissues. Although it does not contain a group which enhances retention of the antibacterial agent on the teeth and soft gum tissue, it is highly effective in retarding plaque and gingivitis.

As employed herein, the phosphonic delivery-enhancing group attaches or substantively, adhesively, cohesively or otherwise bonds the PVPA (carrying the antibacterial agent) to oral (e.g. tooth and gum) surfaces, thereby "delivering" the antibacterial agent to such surfaces.

The PVPA is an anionic polymer comprising a chain or backbone containing repeating vinyl units.

The polyvinylphosphonate may be present in its water-soluble acid form, or salt (including acid salts) form. Salts include the alkali metal, preferably sodium or potassium, or ammonium water-soluble salts. The polymer has an average molecular weight of at least about 1,000, typically about 1,000 to about 1,000,000 and preferably about 6,000 to about 100,000 and most preferably about 6,000 to about 10,000, say about 6,000 to about 8,000. It may be polymerized from vinyl phosphonyl chloride by free radical polymerization in accordance with art recognized technique. The polyvinyl phosphonate is employed in amount of at least about 0.005% by weight to enhance antibacterial effect. It is generally employed in the compositions in approximate weight amounts of 0.05 to 4%, generally about 0.05 to 3%, preferably 0.05 to 2.5%, more preferably 0.1 to 2.5% by weight. Amounts of at least about 1% by weight are typically employed in dentifrice compositions, meaning oral compositions which generally contain a dental abrasive and used in conjunction with brushing of the teeth, e.g. tooth pastes including gels and creams, and powders. Amounts in excess of 4% by weight may be employed for thickening or gelling purposes.

In accordance with the present invention, the orally acceptable vehicle is effective to enable the substantially water-insoluble noncationic antibacterial agent to dissolve in saliva in an effective antiplaque amount. Surface-active agent, flavoring oil or mixture thereof is effective for dissolving the antibacterial agent.

In the oral preparation, an orally acceptable vehicle includes a water-phase with humectant present. In a gel dentifrice, typically containing about 5.30% by weight of a siliceous polishing agent, water is typically present in amount of at least about 3% by weight, generally about 3.35%, and humectant, preferably glycerine and/or sorbitol typically total about 6.5–75% or 80% by weight of the oral gel dentifrice composition. Reference hereto to sorbitol refers to the material typically as available commercially in 70% aqueous solutions.

The gel dentifrices, when the amount of antibacterial agent is about 0.25–0.35% by weight, do not require a further ingredient in the oral vehicle to solubilize the antibacterial agent, although the presence of such solubilizing agent is optional. When the amount of antibacterial agent is below about 0.25% by weight, e.g. about 0.01 up to about 0.25% by weight, solubilizing agent therefore should be present in order to assure sufficient solubilization in saliva for antiplaque effectiveness. When the amount of antibacterial agent is above about 0.35% by weight, e.g. about 0.35 to about 0.5% or more, say 5%, solubilizing agent therefore should be present since otherwise a substantial part of the antibacterial agent could remain insoluble.

When the oral composition is a dentifrice containing about 30–75% by weight of a dentally acceptable polishing agent, the presence of such solubilizing agent is also optional.

When the oral composition is a mouthwash or liquid dentifrice, the oral vehicle desirably includes a nontoxic alcohol in addition to at least one of a surface-active agent and a flavoring oil, each of which assists in dissolving the antibacterial agent. Again the presence of the further solubilizing agent is optional.

When solubilizing agent is present in oral compositions of the instant invention, it is typically in amount of at least about 0.5% by weight being sufficient when the amount of substantially water-insoluble non-cationic antibacterial agent is low, say up to about 0.3% by weight. When higher amounts such as at least about 0.5% by weight of antibacterial agent are present and particularly when siliceous polishing agent is also present in amount of about 5.30% by weight, it is desirable that at least about 5% by weight, typically up to about 20% or more by weight, of the solubilizing agent be present. It is noted that there may be a tendency for the dentifrice to separate into liquid and solid portions when more than about 5% by weight of the solubilizing agent is present.

The agent which is or may be present to assist solubilization of the antibacterial agent in saliva may be incorporated in the water-humectant vehicle. Such solubilizing agents include humectant polyols such as propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate. As used herein, "propylene glycol" includes 1,2-propylene glycol and 1,3-propylene glycol. Significant amounts of polyethylene glycol particularly of molecular weight of 600 or more should be avoided since polyethylene glycol effectively inhibits the antibacterial activity of the noncationic antibacterial agent. For instance, polyethylene glycol (PEG) 600 when present with triclosan in a weight ratio of 25 triclosan:1 PEG 600 reduces the antibacterial activity of triclosan by a factor of about 16 from that prevailing in the absence of the polyethylene glycol.

In accordance with aspects of this invention, oral compositions may be substantially gel in character, such as a gel dentifrice. Such gel oral preparations may contain siliceous dentally polishing material. Preferred polishing materials include silica gel or colloidal silica and complex amorphous alkali metal aluminosilicate.

When visually clear or opacified gels are employed, a polishing agent of colloidal silica, such as those sold under the trademark SYLOID as Syloid 72 and Syloid 74 or under the trademark SANTOCEL as Santocel 100 or alkali metal aluminosilicate complexes (that is, silica containing alumina combined in its matrix) are particularly useful, since they are consistent with gel-like texture and have refractive indices close to the refractive indices of gelling agent-liquid (including water and/or humectant) systems commonly used in dentifrices).

The polishing material is generally present in the oral composition dentifrices such as toothpaste or gel compositions in weight concentrations of about 5% to about 30%.

In the aspect of this invention wherein the oral preparation is a dentifrice, an orally acceptable vehicle including a water-phase with humectant which is preferably glycerine and/or sorbitol is present, wherein water is present typically in amount of about 15-35% or 40% by weight and glycerine and/or sorbitol typically total about 20-75% by weight of the oral preparation dentifrice, more typically about 25-60%. Reference hereto to sorbitol again refers to the material typically as available commercially in 70% aqueous solutions.

In this invention, the oral dentifrice composition may be substantially pasty in character, such as a toothpaste (dental cream), although when siliceous polishing agent is employed (which is not generally the case, since such material is typically not employed in amount above about 30% by weight) it can be gel in character. The vehicle of the oral composition dentifrice contains dentally acceptable polishing material, examples of which polishing materials are water-insoluble sodium metaphosphate, potassium metaphosphate, tricalcium phosphate, dihydrated dicalcium phosphate, anhydrous dicalcium phosphate, calcium carbonate, aluminum silicate, hydrated alumina, silica, bentonite, and mixtures thereof with each other or with hard polishing materials such as calcined alumina and zirconium silicate, material including the particulate thermosetting resins described in U.S. Pat. No. 3,070,510 issued Dec. 15, 1962, such as melamine-phenolic and urea-formaldehydes, and cross-linked polyepoxides and polyesters. Preferred polishing materials include insoluble sodium metaphosphates, dicalcium phosphate and hydrated alumina.

Many of the so-called "water-insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, Pp. 510-511. The forms of insoluble sodium metaphosphate known as Maddrell's salt and Kurrol's salt are further examples of suitable materials. These metaphosphate salts exhibit only a minute solubility in water, and therefore are commonly preferred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali meal metaphosphate is typically employed in powder form of a particle size such that no more than 1% of the material is larger than 37 microns.

Hydrated alumina is an example of a polishing material which is essentially nonionic in nature. Typically, it is small in particle size, i.e., at least about 85% of the particles are smaller than 20 microns and is such as that classified as gibbsite (alpha alumina trihydrate) and normally represented chemically as $Al_2O_3.3H_2O$ or $Al(OH)$.

The average particle size of gibbsite is generally about 6 to 9 microns. A typical grade has the following size distribution:

| Micron | Percent |
| --- | --- |
| <30 | 94-99 |
| <20 | 85-93 |
| <10 | 56-67 |
| <5 | 28-40 |

The polishing material is generally present in the cream paste or gel compositions in weight contents of about 30% to about 75%.

Toothpastes or dental cream dentifrices as well as gel dentifrices typically contain a natural or synthetic thickener or gelling agent in proportions of about 0.1 to about 10%, preferably about 0.5 to about 5%. A suitable thickener is synthetic colloidal magnesium alkali metal silicate complex clay available, for example, as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners or gelling agents or thickeners include Irish moss, iota-carrageenan, gum tragacanth, starch, polyvinylpyrrolidone, hydroxyethylpropyl cellulose, hydroxybutyl methyl cellulose, hydroxypropyl methyl cellulose, hydroxyethyl cellulose (e.g. available as Natrosol), sodium carboxymethyl cellulose, and particularly when siliceous polishing agent is present, colloidal silica such as those available as finely ground Syloid 244 or Sylodent 15.

In the aspect of the present invention wherein the oral composition is a mouthwash or liquid dentifrice, that is, it is substantially liquid in character, the vehicle, particularly in a mouthwash, is typically a water-alcohol mixture. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70 to about 99.9% by weight. The alcohol is a non-toxic alcohol such as ethanol or isopropanol. Humectant such as glycerine and sorbitol may be present in amount of about 10-30% by weight. Liquid dentifrices typically contain about 50-85% of water, may contain about 0.5-20% by weight of non-toxic alcohol and may also contain about 10-40% by weight of humectant such as glycerine and/or sorbitol. Reference here to sorbitol refers to the material typically as available commercially in 70% aqueous solutions. Ethanol is the preferred non-toxic alcohol. The alcohol is believed to assist in dissolving the water-insoluble noncationic antibacterial agent as, it is believed also does flavoring oil.

As indicated, the noncationic antibacterial agent is substantially water-insoluble. However, in a mouthwash or liquid dentifrice of the present invention non-toxic alcohol is often present in addition to at least one of organic surface-active agent and flavoring oil or non-toxic alcohol to aid dissolving the antibacterial agent to assist it to reach soft oral tissue at or near the gums as well as tooth surfaces. Organic surface-active agents and/or flavoring oils may also assist dissolving the antibacterial agents as optional ingredients in oral dentifrice compositions.

Organic surface-active agents are also used in the compositions of the present invention to achieve increased prophylactic action as well as to assist in achieving thorough and complete dispersion of the antiplaque antibacterial agent throughout the oral cavity and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, alkyl alkyl taurines, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-methyl-N-cococyl taurate, N-methyl-N-oleoyl taurate, N-methyl-N-palmitoyl-taurate, N-lauroyl sarcosinate, and the sodium, potassium, and ethanolamine salts of N-lauroyl, N-myristoyl, or N-palmitoyl sarcosine which should be substantially free from soap or similar higher fatty acid material. The taurine compounds particularly assist solution. The use of these sarcosinate compounds in the oral compositions of the present invention can be particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen containing compounds reactive therewith having hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.. Pluronic materials).

Surface active agent, including mixtures thereof, is typically present in amount of about 0.4-5% by weight, preferably about 0.4-0.6% for anionic agents and about 1-2.5%.

When the oral composition is a liquid dentifrice the natural or synthetic thickener or gelling agent as described is typically present in proportions of about 0.1 to about 10%, preferably about 0.5 to about 5%.

Liquid dentifrices may contain a polishing agent. For instance, as described in U.S. Pat. No. 3,506,757 to Salzmann, when about 0.3-2.0% by weight of a polysaccharide of high molecular weight in excess of 1,000,000 containing mannose, glucose, potassium glucuronate and acetyl moieties in the approximate ratio of 2:1:1:1, as suspending and thickening agent is employed in a liquid dentifrice, about 10-20% of a polishing material such as hydrated alumina, dicalcium phosphate dihydrate, calcium pyrophosphate, insoluble sodium metaphosphate, anhydrous dicalcium phosphate, calcium carbonate, magnesium carbonate, magnesium oxide, silica, mixtures thereof, and the like is employed.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, perillartine, AMP (aspartyl phenyl alanine, methyl ester), saccharine and the like. Suitably, flavor and sweetening agents may each or together comprise from about 0.1% to 5% or more of the preparation. Moreover, like the surface-active agent, flavoring oil is believed to aid the dissolving of the antibacterial agent, together with or even in the absence of surface-active agent.

Without being bound to a theory whereby the advantages of this invention are achieved, it is believed that an aqueous, humectant vehicle is normally solubilized in surfactant micelles in the mobile phase (that is, not including gelling agent and polishing agent, if present in a dentifrice formula). The mobile phase solution of dentifrice during use can become diluted with saliva which causes triclosan to resolubilize. Thus, it is found that, even in the absence of a special solubilizing material, for triclosan, when the amount of triclosan is about 0.25% –0.35% by weight and PVPA and vehicle is present. Triclosan and flavor and/or surfactant are in the anterior of the micelle while PVPA is in the exterior. Thus, sufficient triclosan is present to exert an excellent antiplaque effect on the soft tissues at the gum line. Similar remarks apply to other water-insoluble noncationic antibacterial agents herein described.

The oral composition may also contain linear molecularly dehydrated polyphosphate salts employed in the form of their wholly partially neutralized water soluble alkali metal e.g. potassium and preferably sodium) or ammonium salts, and mixtures thereof. Representative examples include sodium hexametaphosphate, sodium tripolyphosphate, disodium diacid, trisodium monoacid and tetrasodium pyrophosphates, the corresponding potassium salts and the like, including mixtures thereof. When present, they are preferably employed in the oral compositions in approximate weight amounts of 0.1% to 3% typically 1 to 2.5% more typically 1.5 to 2%. Oral compositions containing polyphosphate and PVPA are described in commonly assigned U.S. Pat. No. 5,094,844, issued Mar. 10, 1992.

When polyphosphate is present, a ratio of PVPA to polyphosphate ion of about 1:6 to about 2.7:1 can be particularly desirable.

Various other materials may be incorporated in the oral preparations of this invention such as whitening agents, preservatives, silicones, chlorophyll compounds and/or ammoniated material such as urea, diammonium phosphate, and mixtures thereof. Additional anticalculus agent such as azacycloheptane-2,2 diphosphonate, may also be employed, typically in amount of about 0.1–5% by weight. These adjuvants, where present, are incorporated in the preparations in amounts which do not substantially adversely affect the properties and characteristics desired. Significant amounts of zinc, magnesium and other metal salts and materials, which are generally soluble and which would complex with active components of the instant invention are to be avoided.

The oral composition may also contain a source of fluoride ions or fluorine-providing component as anticaries agent in amount sufficient to supply about 25 ppm. to 5,000 ppm. of fluoride ions. This component also inhibits enzymatic degration of polyphosphate, if present. These compounds may be slightly soluble in water or more preferably fully water-soluble. They are characterized by ability to release fluoride ions in water and by substantial freedom from undesired reaction with other compounds of the oral preparation. Among these materials are inorganic fluoride salts, such as soluble alkali metal fluorides, for example, sodium fluoride, potassium fluoride and ammonium fluoride, calcium fluoride, a copper fluoride such as cuprous fluoride, zinc fluoride, barium fluoride, sodium fluorosilicate, ammonium fluorosilicate, sodium fluorozirconate, ammonium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005 to about 3.0% in the preparation. In a dentifrice preparation, e.g. dental gel an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be present in an amount of about 0.1–3%, more typically about 0.76%.

It will be understood that, as is conventional, the oral preparations are to be sold or otherwise distributed in suitable labelled packages. Thus a dentifrice gel will usually e in a collapsible tube typically aluminum, lined lead or plastic, or the squeeze, pump or pressurized dispenser for metering out the contents, having a label describing it, in substance, as a dentifrice gel or the like.

In the preferred practice of this invention, an oral composition of the present invention is preferably applied regularly to dental enamel and soft oral tissues, particularly at or near the gum line, such as every day or every second or third day or preferably from 1 to 3 times daily, at a pH of about 4.5 to about 9 or 10, generally abut 5.5 to about 8, preferably about 6 to 8 and most preferably about 6.5 to about 7.5, for at least 2 weeks up to 8 weeks or more up to lifetime. Even at such pH below 5 enamel is not decalcified or otherwise damaged. The pH can be controlled with acid (e.g. citric acid or benzoic acid) or base (e,g, sodium hydroxide) or buffered as with sodium citrate, benzoate, carbonate or bicarbonate, disodium hydrogen phosphate, sodium dihydrogen phosphate, etc.).

The compositions of this invention can be incorporated in lozenges, or in chewing gum or other products, e.g. by stirring into a warm gum base or coating the outer surface of a gum base, illustrative of which may be mentioned gelating, rubber latex, vinylite resins, etc., desirably with conventional plasticizers or softeners, sugar or other sweeteners or carbohydrates such as glucose, sorbitol and the like.

The following examples are further illustrative of the effective compositions of the present invention, but it is understood that the invention is not limited thereto. All amounts and proportions referred to herein and in the appended claims are by weight, unless otherwise indicated.

EXAMPLE 1

The following mouthrinses are prepared:

| Ingredients | Parts | | | |
|---|---|---|---|---|
| | A Placebo | B PVPA | C Triclosan | D Triclosan & PVPA |
| Sorbitol (70%) | 20 | 20 | 20 | 20 |
| Glycerine | 10 | 10 | 10 | 10 |
| Propylene Glycol | 7 | 7 | 7 | 7 |
| Ethanol | 10 | 10 | 10 | 10 |
| Triclosan | — | — | 0.06 | 0.06 |
| PVPA | — | 3.00 | — | 3.00 |
| Avg. M.W. 6000–8000 | | | | |
| Sodium Fluoride | 0.05 | 0.05 | 0.05 | 0.05 |
| Flavor | 0.25 | 0.25 | 0.25 | 0.25 |
| Water | Q.S. to 100 | Q.S. to 100 | Q.S. to 100 | Q.S. to 100 |
| Sodium Lauryl Sulphate | 0.25 | 0.25 | 0.25 | 0.25 |

A clinical test is conducted with ten persons, aged 24–40 years (mean 29.5), all being free from signs of destructive periodontal disease and who have not been on systemic antibiotic therapy during the 6 months preceding this study. During a preparatory period of two weeks the participants are exposed to professional plaque control measures and are given repeated instructions in self performed plaque control measures. At the end of this preparatory period, each participant receives a full professional tooth cleaning and then abstains from all mechanical tooth cleaning efforts during the course of the next four days. They rinse, however, twice daily, for one minute each time with 10 ml of the test solution. On the fourth day the ten subjects are clinically examined. Immediately following the examinations, they are given professional tooth cleaning and again follow the self performed plaque control measures for 10 days. The participants are then given professional tooth cleaning after which an additional four day test period is initiated. Thus, each person is his own control.

The accounts follow, clearly demonstrating synergistic reduction plaque with Triclosan and PVPA:

| Treatment | N | Mean Plaque Index/Tooth | % Reduction |
|---|---|---|---|
| Placebo Rinse - A | 10 | 1.46 ± 0.12 | — |
| 3% PVPA Rinse - B | 10 | 1.2 ± 0.16 | 7 |
| 0.06% Triclosan Rinse - C | 10 | 0.85 ± 0.20 | 41 |
| 0.06% Triclosan + 3% PVPA - D | 10 | 0.56 ± 0.18 | 61* |

"N" is Number of participants
*Combination is significantly (P≦0.01) more effective than either PVPA or Triclosan

EXAMPLE 2

The following dentifrice are prepared:

| | Parts | |
|---|---|---|
| | A | B |
| Glycerine | 10.00 | — |
| Propylene Glycol | — | 10.00 |
| Sorbitol (70%) | 25.00 | 25.00 |
| Iota carrageenan | 0.60 | 0.60 |
| PVPA (Avg. M.W. 8000) | 2.00 | 2.00 |
| Sodium Saccharin | 0.40 | 0.40 |
| Sodium Fluoride | 0.243 | 0.243 |
| Sodium Hydroxide (50%) | 1.00 | 1.00 |
| Titanium Oxide | 0.50 | 0.50 |
| Silica Polishing Agent (Zeodent 113) | 20.00 | 20.00 |
| Silica Thickener (Sylox 15) | 5.50 | 5.50 |
| Sodium Lauryl Sulfate | 2.00 | 2.00 |
| Water | 31.507 | 31.507 |
| Triclosan | 0.30 | 0.30 |
| Flavor Oil | 0.95 | 0.95 |

EXAMPLE 3

The following liquid phase dentifrice is prepared:

| Ingredients | Parts |
|---|---|
| Sorbitol (70% solution) | 30.0 |
| Glycerol | 9.5 |
| Propylene Glycol | 0.5 |
| SLS | 20.0 |
| NaF | 0.243 |
| Flavor Oil | 0.95 |
| Triclosan | 0.3 |
| PVPA (Avg. M.W. 8000) | 2.00 |
| Water | 56.507 |

EXAMPLE 4

Dentifrices are prepared having the following formulas:

| | Parts | | |
|---|---|---|---|
| | A | B | C |
| Propylene Glycol (1.2) | 10.00 | 10.00 | 10.00 |
| Iota Carrageenan | 0.75 | 0.75 | 0.75 |
| PVPA (Avg. M.W. 6000-8000) | 2.00 | 2.00 | 2.50 |
| Tetrasodium Pyrophosphate | — | 2.00 | 2.00 |
| Titanium Dioxide | 0.50 | 0.50 | 0.50 |
| Sorbitol (70%) | 30.00 | 30.00 | 30.00 |
| Sodium Fluoride | 0.332 | 0.332 | 0.332 |
| Sodium Saccharin | 0.40 | 0.40 | 0.40 |
| Silica Thickener (Sylodent 15) | 3.00 | 3.00 | 3.00 |
| Silica Polishing Agent (Zeodent 113) | 20.00 | 20.00 | 20.00 |
| Triclosan | 0.20 | 0.20 | 0.20 |
| Sodium Lauryl Sulfate | 2.00 | 2.00 | 2.00 |
| Flavor Oil | 0.95 | 0.95 | 0.95 |
| Ethyl Alcohol | 1.00 | 1.00 | 1.00 |
| Water | QS to 100.00 | QS to 100.00 | QS to 100.00 |

EXAMPLE 5

The following dentifrice is prepared:

| Dentifrice | Parts |
|---|---|
| Propylene Glycol | 10.00 |
| Iota Carrageenan | 0.60 |
| Sorbitol (70%) | 25.00 |
| Sodium Saccharin | 0.40 |
| Sodium Fluoride | 0.243 |
| Titanium Dioxide | 0.50 |
| PVPA (AVG M.W. 6000-8000) | 2.00 |
| Water | 29.157 |
| NaOH (50%) | 2.00 |
| Zeodent 113 (Silica Polishing Agent) | 20.00 |
| Sylodent 15 (Silica Thickener) | 5.50 |
| Flavor | 1.10 |
| Triclosan | 0.50 |
| Sodium Lauryl Sulfate | 2.00 |
| Ethanol | 1.00 |

EXAMPLE 6

The following dentifrice is prepared:

| | Parts |
|---|---|
| Propylene Glycol | 10.00 |
| Sorbitol (70%) | 25.00 |
| Sodium Carboxymethyl Cellulose | 0.60 |
| Sodium Saccharin | 0.40 |
| Sodium Fluoride | 0.243 |
| Silica Polishing Agent (Zeodent 113) | 20.00 |
| Silica Thickener (Sylox 15) | 5.50 |
| Water | 28.857 |
| PVPA (Avg. M.W. 6000-8000) | 2.00 |
| Triclosan | 0.30 |
| Titanium Dioxide | 0.50 |
| Sodium Lauryl Sulfate | 2.50 |
| Flavor | 1.10 |
| Ethyl Alcohol | 1.00 |
| Sodium Hydroxide (50%) | 2.00 |

Likewise, when other solubilizing agents, particularly dipropylene glycol, hexylene glycol, methyl cellosolve, ethyl cellosolve, olive oil, castor oil, petrolatum, amyl acetate, ethyl acetate, glycerol tristerate and benzyl benzoate, replace propylene glycol, triclosan is effectively delivered to soft oral tissues. Further, similar results are obtained with propylene glycol or other solubilizing agents are omitted from the toothpaste containing 0.3% triclosan.

EXAMPLE 7

The following dentifrices are prepared:

| | Parts | |
|---|---|---|
| | A | B |
| Glycerine | — | 20.00 |
| Propylene Glycol | 10.00 | 0.50 |
| Sorbitol (70%) | 25.00 | 19.50 |
| Sodium Carboxymethyl Cellulose | — | 1.10 |
| Iota Carrageenan | 0.600 | — |

-continued

|  | Parts | |
|---|---|---|
|  | A | B |
| Sodium Saccharin | 0.40 | 0.30 |
| Sodium Fluoride | 0.243 | 0.243 |
| Silica Polishing Agent (Zeodent 113) | 20.00 | 20.00 |
| Silica thickener (Sylox 15) | 5.50 | 3.00 |
| Water | 28.757 | 15.307 |
| PVPA (Avg. M.W. 6000-8000) | 2.00 | 2.00 |
| Triclosan | 0.50 | 0.30 |
| Titanium Dioxide | 0.50 | 0.50 |
| Sodium Lauryl Sulfate | 2.50 | 2.00 |
| Flavor | 1.10 | 0.95 |
| Ethanol | 1.00 | — |
| Sodium Hydroxide (50%) | 2.00 | 1.60 |

In the foregoing examples, improved results are also obtained by replacing triclosan with other antibacterial agents herein described, such as phenol, thymol, eugenol and 2,2' methylene bis (4-chloro-6-bromophenol).

EXAMPLE 8

The following dentifrices are prepared:

|  | Parts | | |
|---|---|---|---|
|  | A | B | C |
| Alpha Alumina Trihydrate | 48.00 | 48.00 | 48.00 |
| Propylene Glycol | — | 0.50 | 0.50 |
| Sorbitol (70%) | 21.70 | 21.70 | 21.70 |
| PVPA (Avg. M.W. 6000-8000) | 2.00 | 2.00 | 2.00 |
| Sodium Lauryl Sulfate | 2.00 | 2.13 | 2.13 |
| Sodium Saccharine | 0.30 | 0.30 | 0.30 |
| Sodium Hydroxide (50%) | 1.20 | 1.20 | 1.20 |
| Flavor | 0.95 | 0.95 | 0.95 |
| Irish Moss | 1.00 | — | — |
| Sodium carboxymethyl cellulose | — | 1.00 | 1.00 |
| Sodium monofluorophosphate | 0.76 | 0.76 | 0.76 |
| Titanium Dioxide | — | 0.50 | 0.50 |
| Triclosan | 0.30 | 0.30 | 0.30 |
| Water | QS to 100.00 | QS to 100.00 | QS to 100.00 |

EXAMPLE 9

The following dentifrices are prepared:

|  | Parts | |
|---|---|---|
| Glycerine | 22.00 | 10.00 |
| Sorbitol (70%) | — | 17.00 |
| Sodium Carboxymethyl cellulose | 1.00 | 1.00 |
| PVPA (Avg. M.W. 6000-8000) | 2.00 | 2.00 |
| Sodium Saccharin | 0.20 | 0.20 |
| Sodium Benzoate | 0.50 | 0.50 |
| Sodium Monofluorophosphate | 0.76 | 0.76 |
| Dicalcium Phosphate Dihydrate | 48.76 | 48.76 |
| Triclosan | 0.30 | 0.30 |
| Sodium Lauryl Sulfate | 1.20 | 1.20 |
| Flavor | 0.89 | 0.89 |
| Water | QS to 100.00 | QS to 100.00 |

EXAMPLE 10

The following antiplaque dentifrice is prepared:

|  | Parts |
|---|---|
| Glycerine | 15.00 |
| Propylene Glycol | 2.00 |
| Sodium Carboxymethyl cellulose | 1.50 |
| Water | 22.69 |
| PVPA (Avg. M.W. 6000-8000) | 2.00 |
| Sodium Monofluorophosphate | 0.76 |
| Sodium Saccharin | 0.30 |
| Insoluble Sodium Metaphosphate | 47.00 |
| Titanium Dioxide | 0.50 |
| Sodium Lauryl Sulfate | 2.00 |
| Triclosan | 0.30 |
| Flavor | 0.95 |

In the foregoing examples triclosan can be effectively replaced with each of phenol, 2,2'-methylene bis (4-chloro-6-bromophenol), eugenol and thymol.

EXAMPLE 11

Dentifrice Mobile Phase Containing Triclosan

| Components | Parts | |
|---|---|---|
| Sorbitol (70%) | 50.00 | 40.00 |
| Water | 40.48 | 50.48 |
| PVPA (Avg. A.W. 6000-8000) | 2.00 | 2.00 |
| NaOH (50%) | 1.33 | 1.33 |
| Saccharin | 0.40 | 0.40 |
| Sodium Fluoride | 0.32 | 0.32 |
| Flavor Oil | 1.47 | 1.47 |
| Sodium Lauryl Sulfate | 3.33 | 3.33 |
| Triclosan | 0.67 | 0.67 |

The concentration of the above mobile phases are 75% of finished dentifrice level to reflect 25% level of polishing agent to make a complete dentifrice.

EXAMPLE 12

The mouthrinses below are prepared:

|  | A Parts | B Parts | C Parts | D Parts | E Parts |
|---|---|---|---|---|---|
| PVPA (Avg. M.W. 6000-8000) | 0.25 | 0.25 | 0.25 | 0.25 | 0.25 |
| Glycerine | 15.00 | 10.00 | 15.00 | 10.00 | 15.00 |
| Ethanol | — | — | 12.50 | 12.50 | — |
| Propylene Glycol | — | 5.00 | — | 5.00 | — |
| Pluronic F108-(Polyoxhtylene/Polyoxypropylene Block Copolymer) | 2.00 | 2.00 | 2.00 | 2.00 | 2.00 |
| Sodium Lauryl Sulfate | — | — | 0.20 | 0.20 | 0.20 |
| Triclosan | 0.10 | 0.10 | 0.06 | 0.06 | 0.03 |
| Flavoring Oil | 0.40 | 0.40 | 0.40 | 0.40 | 0.40 |
| Water | QS to 100.00 | QS to 100.00 | QS to 100.00 | QS to 100.00 | QS to 100.00 |

EXAMPLE 13

The following liquid dentifrices are prepared:

|  | A Parts | B Parts | C Parts |
|---|---|---|---|
| Glycerine | 20.0 | 20.0 | — |
| PVPA (Avg. M.W. 6000—8000) | 0.3 | 0.3 | 0.3 |
| Polysaccharide of high molecular weight, the molecule containing mannose, glucose, potassium glucuronate and acetyl moieties in the approximate molar ratio of 2:1:1:1 | 0.8 | — | 1.0 |
| Sodium benzoate | 0.5 | 0.5 | 0.5 |
| Saccharine sodium | 0.5 | 0.5 | 0.5 |
| Water | 61.3 | 73.1 | 71.6 |
| Sodium lauryl sulfate | 3.0 | 3.0 | 3.0 |
| Insoluble sodium metaphosphate | 10.0 | — | 10.0 |

|  | A Parts | B Parts | C Parts |
|---|---|---|---|
| Anhydrous dicalcium phosphate | 1.0 | — | 2.5 |
| Flavoring Oil | 2.5 | 2.5 | 2.5 |
| Ethyl alcohol | — | — | 10.0 |
| Triclosan | 0.1 | 0.1 | 0.1 |

In the foregoing Examples, improved results are also achieved when triclosan is replaced with each of phenol, 2,2'-methylene bis (4-chloro-6-bromophenol), eugenol and thymol.

This invention has been described with respect to certain preferred embodiments and it will be understood that modifications and variations thereof obvious to those skilled in the art are to be included within the preview of this application and the scope of the appended claims.

I claim:

1. An oral composition comprising an effective antiplaque amount of about 0.01%–5% of a substantially water insoluble noncationic antibacterial agent, 0.005%–4% by weight of polyvinyl phosphonate having recurring groups

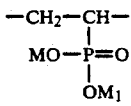

and average molecular weight of at least about 1,000 wherein M and M₁ are hydrogen alkali metal or ammonium and wherein M and M₁ are the same or different, and an orally acceptable vehicle comprising at least one of a surface-active agent or a flavoring oil effective to enable the said antibacterial agent to dissolve in saliva in effective antiplaque amount, said polyvinyl phosphonate enhancing the antibacterial effect of said antibacterial agent to inhibit plaque formation.

2. The oral composition claim in claim 1, in which the said oral composition is a dentifrice comprising about 5–30% by weight of a siliceous polishing agent and the said antibacterial agent is present in amount of about 0.25–0.35% by weight.

3. The oral composition claimed in claim 1, in which the said oral composition is a dentifrice comprising about 5–30% by weight of a siliceous polishing agent, the said antibacterial agent is present in amount of about 0.01–5% by weight and the said oral composition comprises a solubilizing material in amount to assist dissolving the said antibacterial agent in saliva.

4. The oral composition claimed in claim 3, in which the said antibacterial agent is present in amount of about 0.05% up to below about 0.25% by weight.

5. The oral composition claimed in claim 3, in which the said antibacterial agent is present in amount of above about 0.35% up to about 5% by weight.

6. The oral composition claimed in claim 5, in which the said antibacterial agent is present in amount of above about 0.35% up to about 0.5% by weight.

7. The oral composition claimed in any one of claims 1 to 6 in which the said oral composition is a dentifrice comprising about 30–75% by weight of a dentally acceptable water-insoluble polishing agent.

8. The oral composition claimed in claim 1, in which the said oral composition is a mouthwash or liquid dentifrice and the said orally acceptable vehicle is an aqueous vehicle wherein there is present a non-toxic alcohol.

9. The oral composition claimed 1 in which there is present surface-active agent in amount of about 0.5–5% by weight.

10. The oral composition claimed 1 in which there is present flavoring oil in amount of about 0.1–5% by weight.

11. The oral composition claimed in claim 8 in which the said composition is a mouthwash and the said aqueous vehicle contains ethanol and the weight ratio of water to ethanol is from about 1:1 to about 20:1.

12. The oral composition claimed in claim 8 or claim 11 in which the said oral composition is a liquid dentifrice containing about 0.3–2 0% by weight of a polysaccharide of high molecular weight in excess of 1,000,000 containing mannose, glucose, potassium glucuronate and acetyl moieties in the approximate ratio of 2:1:1:1, as suspending and thickening agent and about 10–20% by weight of a polishing material.

13. The oral composition claimed in any one of claims 1 to 12 in which the said antibacterial agent is selected form the group consisting of halogenated diphenyl ethers, halogenated salicylanilides, benzoic esters, halogenated carbanilides and phenolic compounds.

14. The oral composition claimed in claim 13 in which the said antibacterial agent is a halogenated diphenyl ether.

15. The oral composition claimed in claim 14 in which the said halogenated diphenyl ether is 2,4,4'-trichloro-2''-hydroxyphenyl ether.

16. The oral composition claimed in any one of claims 1 to 15 in which a solubilizing agent is present in amount of about 0.5 to 50% by weight and is selected from the group consisting of propylene glycol, dipropylene glycol, hexylene glycol, methyl cellosolve, ethyl cellosolve, vegetable oil and was containing at least about 12 carbon atoms, amyl acetate, ethyl acetate, glyceryl tristerate and benzyl benzoate.

17. The oral composition dentifrice claimed in claim 16 in which the solubilizing agent is propylene glycol and is present in amount of about 0.5% by weight.

18. The oral composition in the form of a dentifrice claimed claim 1 wherein about 30–70% by weight of a polishing agent is present which is selected from the group consisting of sodium metaphosphate, tri-calcium phosphate, dihydrated dicalcium phosphate, anhydrous dicalcium phosphate, anhydrous dicalcium phosphate, calcium pyrophosphate, magnesium orthophosphate, trimagnesium phosphate, calcium carbonate, aluminum silicate, hydrated alumina, silica, bentonite and mixtures thereof.

19. The oral composition dentifrice claimed in claim 18 wherein said polishing agent is dicalcium phosphate dihydrate or hydrated alumina.

20. The oral composition claimed in any one of claims 1 to 19 wherein said polyvinyl phosphonate has an average molecular weight of about 1,000 to about 1,000,000 and is present in amount of about 0.005–4% by weight.

21. The oral composition claimed in claim 20 in which the said PVPA copolymer has a molecular weight of about 6,000 to about 100,000.

22. The oral composition claimed in claim 21 in which said PVPA copolymer was a molecular weight of about 6,000 to about 8,000.

23. The oral composition claimed in claim 20 said polyvinyl phosphonate is present in amount of about 0.05–3% by weight.

24. A composition claimed in claim 23 in which said polyvinyl phosphonate is present in amount of about 0.1–2.5% by weight.

25. A method of inhibiting dental plaque comprising applying to tooth and soft gum surfaces the oral composition claimed in any one of claims 1 to 19.

* * * * *